(12) United States Patent
Inskeep

(10) Patent No.: US 7,633,611 B2
(45) Date of Patent: Dec. 15, 2009

(54) METHOD AND APPARATUS FOR TESTING IMAGER DEVICES USING A CENTER TURNING OPTIC

(75) Inventor: Dustin D. Inskeep, Boise, ID (US)

(73) Assignee: Aptina Imaging Corporation, Grand Cayman (KY)

( * ) Notice: Subject to any disclaimer, the term of this patent is extended or adjusted under 35 U.S.C. 154(b) by 406 days.

(21) Appl. No.: 11/458,720

(22) Filed: Jul. 20, 2006

(65) Prior Publication Data

US 2008/0018885 A1      Jan. 24, 2008

(51) Int. Cl.
*G01N 21/00* (2006.01)
(52) U.S. Cl. ............... 356/237.1; 356/237.2; 356/237.5
(58) Field of Classification Search .... 356/237.1–237.5
See application file for complete search history.

(56) References Cited

U.S. PATENT DOCUMENTS

| | | | | |
|---|---|---|---|---|
| 5,034,618 | A * | 7/1991 | Akeel et al. | 250/559.33 |
| 5,504,630 | A * | 4/1996 | Hansen | 359/856 |
| 6,335,824 | B1 * | 1/2002 | Overbeck | 359/368 |
| 6,586,750 | B2 * | 7/2003 | Montagu et al. | 250/458.1 |
| 7,312,919 | B2 * | 12/2007 | Overbeck | 359/368 |
| 2002/0154396 | A1 * | 10/2002 | Overbeck | 359/368 |

* cited by examiner

*Primary Examiner*—Michael P Stafira
(74) *Attorney, Agent, or Firm*—Dickstein Shapiro LLP

(57) ABSTRACT

An optical test system includes a light source, a first turning optic, and a second turning optic. The second turning optic is positioned proximate the light source and is operable to direct light from the light source to the first turning optic. The first turning optic is further operable to direct light from the second turning optic to illuminate one of a plurality of test regions for receiving devices under test. At least one of the first and second turning optics is movable to align the light generated by the light source with a selected test region.

32 Claims, 7 Drawing Sheets

METHOD AND APPARATUS FOR TESTING IMAGER DEVICES USING A CENTER TURNING OPTIC

CROSS-REFERENCE TO RELATED APPLICATIONS

Not applicable.

STATEMENT REGARDING FEDERALLY SPONSORED RESEARCH OR DEVELOPMENT

Not applicable

BACKGROUND OF THE INVENTION

The present invention relates generally to optical imager manufacturing and, more particularly, to a method and apparatus for testing imager devices using a center turning optic.

There are a number of different types of semiconductor-based imagers, including charge coupled devices (CCDs), photo diode arrays, charge injection devices and hybrid focal plane arrays. CCDs are often employed for image acquisition for small size imaging applications. CCDs are also capable of large formats with small pixel size and they employ low noise charge domain processing techniques. However, CCD imagers have a number of disadvantages. For example, they are susceptible to radiation damage, they exhibit destructive read out over time, they require good light shielding to avoid image smear and they have a high power dissipation for large arrays.

Because of the inherent limitations in CCD technology, there is an interest in complementary metal oxide semiconductor (CMOS) imagers for use as low cost imaging devices. A fully compatible CMOS sensor technology enabling a higher level of integration of an image array with associated processing circuits is beneficial to many digital applications such as, for example, in cameras, scanners, machine vision systems, vehicle navigation systems, video telephones, computer input devices, surveillance systems, auto focus systems, star trackers, motion detection systems, image stabilization systems, and data compression systems for high-definition television.

After an imager has been manufactured, a test apparatus is used to verify the proper functionality of the imager. A light source in the test apparatus provides collimated light that is directed over imager devices that are mounted to a test circuit board. The imager devices may be in the form of packed or unpackaged die, depending on the point in the production flow at which they are functionally tested. When the imager devices are illuminated by the light source, the test circuit board runs one or more test procedures that operate the imager devices to capture the image provided by the light source and determine if the capture was accurate.

Conventional light sources are sized to illuminate multiple imager devices in parallel. Such parallel testing is limited by the effective area that a light source can produce consistent, uniform light to the devices as well as how closely the devices can be mechanically mounted to the test circuit board. Currently available test apparatus allow parallel testing of about four imager devices using a light source capable of producing collimated light over an approximately 38 mm diameter region. Increasing the size of the light source to cover an approximately 77 mm diameter region to allow parallel testing of eight imager devices would result in an extremely costly test apparatus. For example, a single light source for such an apparatus is estimated to cost over $100,000.

Due to the constraints of the light source the number of imager devices that can be tested in parallel is limited. Each set of four devices tested must be unloaded and a new set of devices must be mounted to the test circuit board between tests. Hence, the time required to test a group of devices is significant.

This section of this document is intended to introduce various aspects of art that may be related to various aspects of the present invention described and/or claimed below. This section provides background information to facilitate a better understanding of the various aspects of the present invention. It should be understood that the statements in this section of this document are to be read in this light, and not as admissions of prior art. The present invention is directed to overcoming, or at least reducing the effects of, one or more of the problems set forth above.

BRIEF DESCRIPTION OF THE SEVERAL VIEWS OF THE DRAWINGS

The invention will hereafter be described with reference to the accompanying drawings, wherein like reference numerals denote like elements, and.

Figure 1:
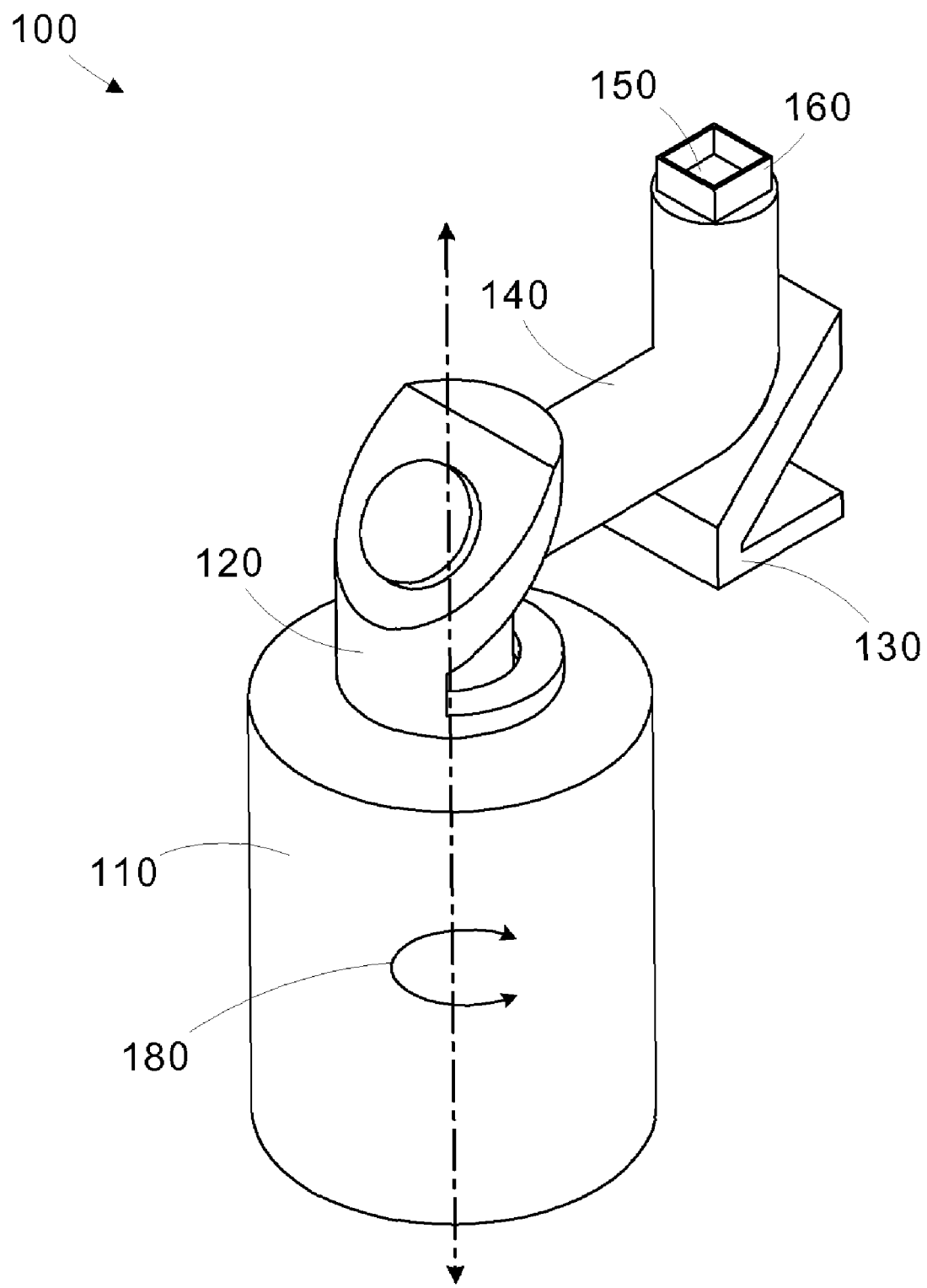
FIG. 1 is a diagram of an optical test system in accordance with an illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

One or more specific embodiments of the present invention will be described below. It is specifically intended that the present invention not be limited to the embodiments and illustrations contained herein, but include modified forms of those embodiments including portions of the embodiments and combinations of elements of different embodiments as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the present invention unless explicitly indicated as being "critical" or "essential."

The present invention will now be described with reference to the attached figures. Various structures, systems and devices are schematically depicted in the drawings for purposes of explanation only and so as to not obscure the present invention with details that are well known to those skilled in the art. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Figure 2:
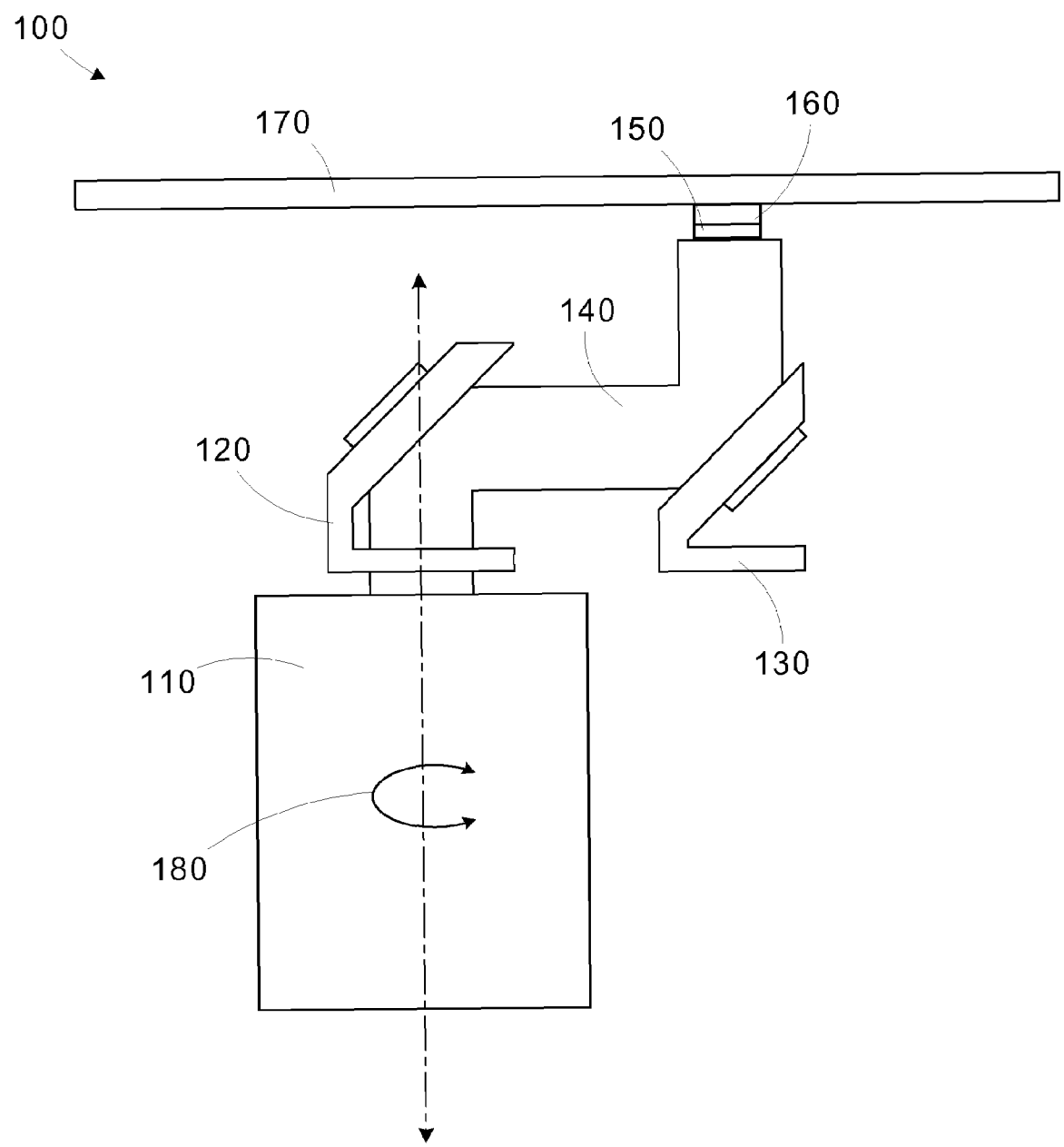
FIG. 2 is a side view of the optical test system of FIG. 1.

Referring now to the drawings wherein like reference numbers correspond to similar components throughout the several views and, specifically, referring to FIGS. 1 and 2, the present invention shall be described in the context of an optical test system 100. The optical test system 100 includes a light source 110, a center turning optic 120, and a remote turning optic 130. In general, a light beam 140 generated by the light source 110 is reflected by the center turning optic 120 to impinge upon the remote turning optic 130, which in turn reflects the light to illuminate an imager device 150 mounted in a socket 160 of a test circuit board 170 (shown in FIG. 2). In the illustrated embodiment the center turning optic 120 and the remote turning optic 130 are 45° turning optics, however, other reflection angles may be used depending on the particular orientation of the socket 160 with respect to the light source 110. Although the invention is described as it may be implemented for illuminating imager devices 150, the application of the present invention is not limited only to imager devices 150 (e.g., CMOS or CCD imagers). Rather, the optical test system 100 may be used for illuminating and testing other types of devices.

In one embodiment, the center turning optic 120 is rotatable about an axis 180 to allow the alignment of the center turning optic 120 with the remote turning optic 130 to illuminate the imager device 150. Generally, a rotational movement is chosen for compactness, however, the application of the present invention is not limited to the rotary examples provided herein. For example, the center turning optic 120 may be movable in a linear fashion to align with the remote turning optic 130. In yet another example, the movable aspects of the turning optics 120, 130 may be reversed. For example, the center turning optic 120 may be fixed, and the remote turning optic 130 may be movable in a linear fashion to align with the imager device 150.

As will be described in greater detail below, the optical test system 100 may be used to test multiple imager devices 150 mounted to the test circuit board 170 by positioning the center turning optic 120 and/or remote turning optic 130 to illuminate the individual imager devices 150. In some embodiments, the center turning optic 120 may be fixed to the light source 110, and the light source 110 may move along with the center turning optic 120 to achieve alignment with the remote turning optic 130. In the illustrated embodiment, the light source 110 illuminates an area approximate 20 mm in diameter. Of course, the diameter of the light beam 140 generated by the light source 110 may vary depending on the size of the imager device 150 being illuminated. Due to its relatively small size, the light source 110 is inexpensive as compared to the light sources capable of generating larger diameter light beams.

Figure 3:
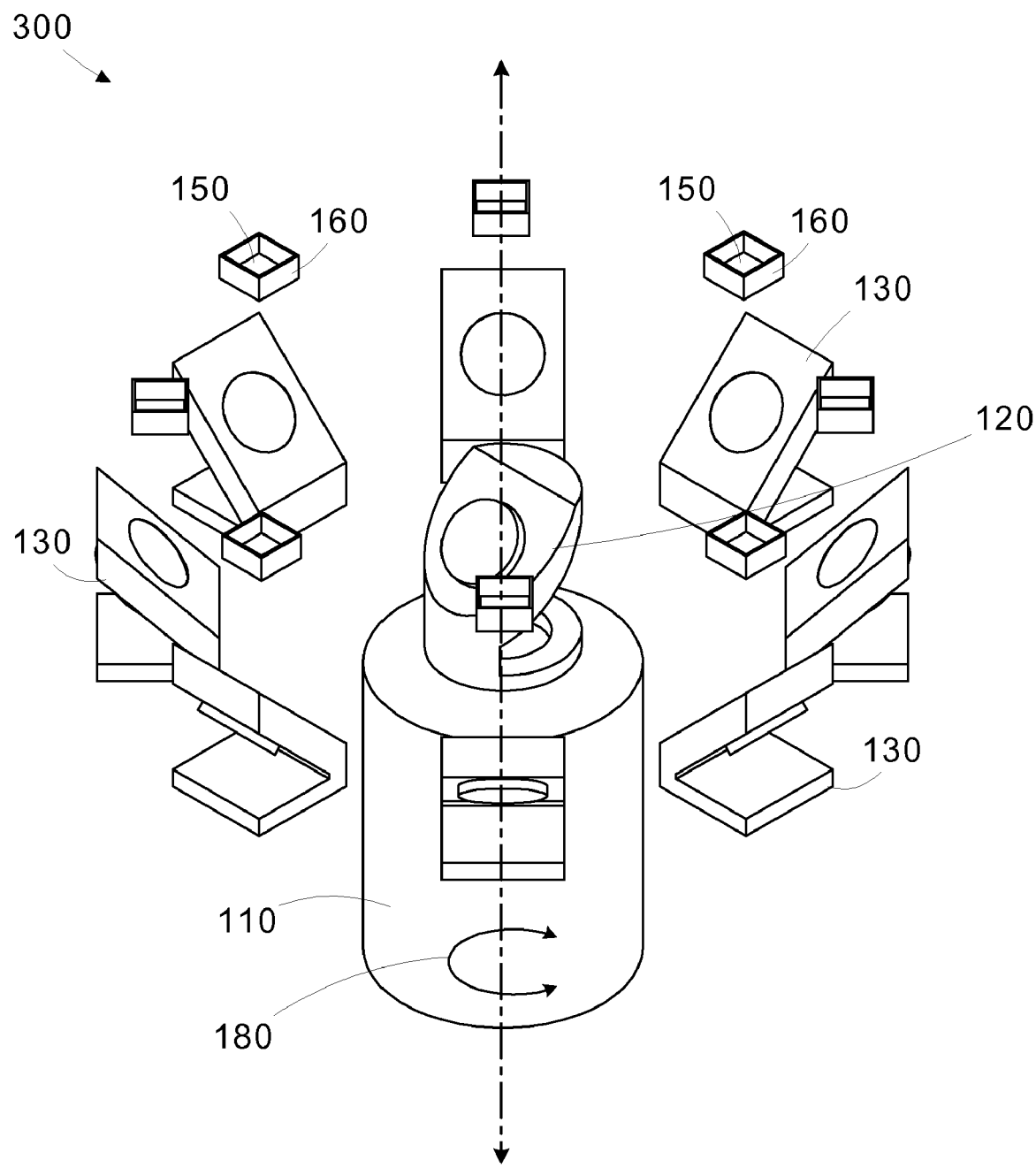
FIG. 3 is a diagram of an optical test system including a plurality of fixed remote turning optics positioned about a central turning optic.

Turning now to FIG. 3, a diagram of one embodiment of an optical test system 300 is provided. The optical test system 300 includes multiple remote turning optics 130 disposed radially about the axis of rotation 180 of the center turning optic 120. The sockets 160 to which imager devices 150 are mounted are aligned with each of the remote turning optics 130. The remote turning optics 130 may be mounted to a frame (such as the frame 420 shown in FIG. 4) in fixed positions beneath the sockets 160. Hence, the position of the center turning optic 120 may be varied to align the light beam 140 with the remote turning optic 130 below the socket 160 of a selected imager device 150 under test. In this manner multiple devices (e.g., 8 as illustrated) may be tested concurrently (i.e., the test periods at least partially overlap). The imager devices 150 are illuminated in a serial fashion, but the data processing tasks that occur after an image has been acquired may proceed in parallel. For instance, after an image has been captured by a first imager device 150, the center turning optic 120 may be aligned with a second imager device 150, which in turn captures another image. This second capture may be performed while the functional testing of the first imager device 150 is being performed by the test circuit board 170.

Figure 4:
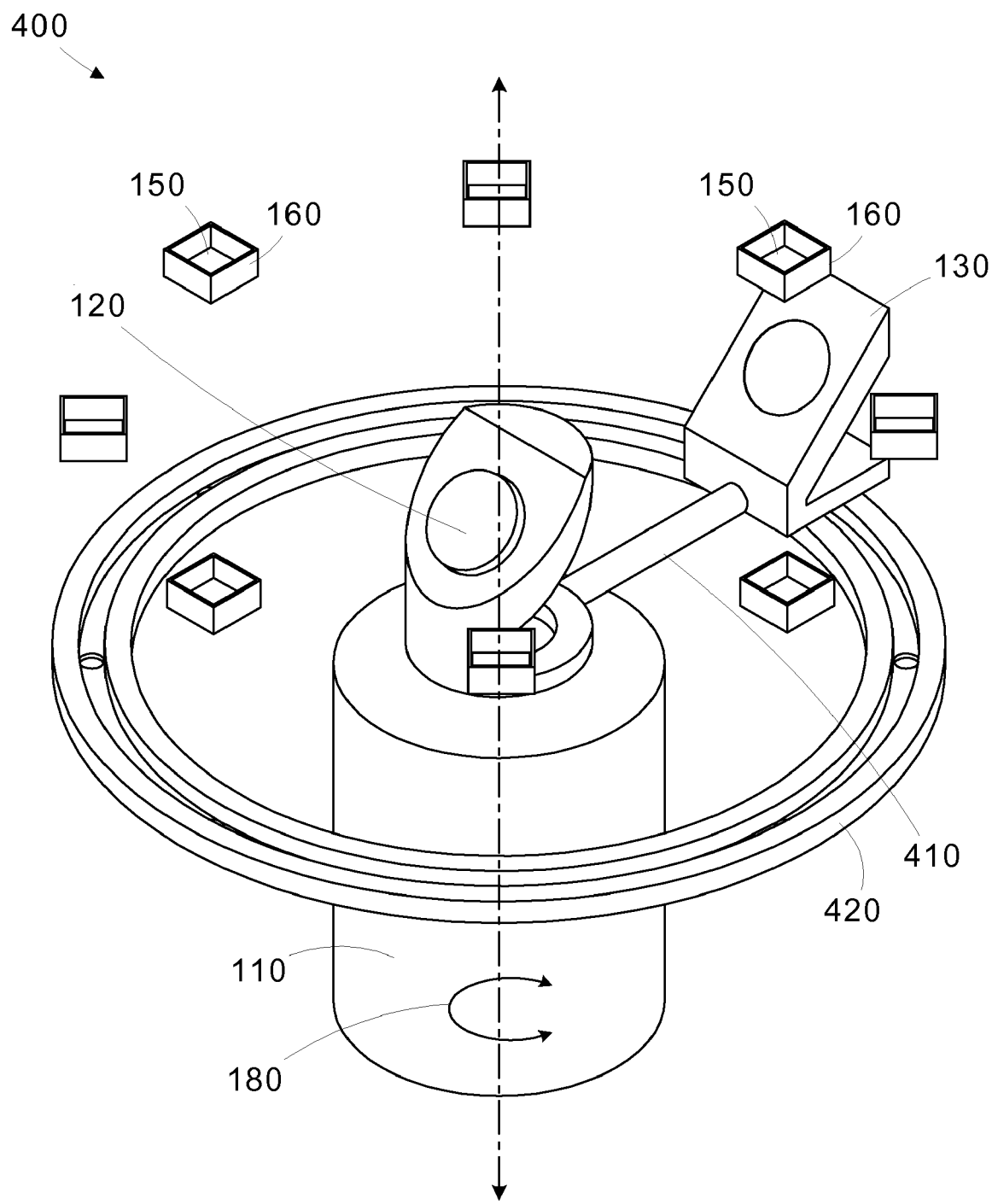
FIG. 4 is a diagram of an optical test system including a remote turning optic coupled to a central turning optic.

In another embodiment illustrated in FIG. 4, an optical test system 400 includes a single remote turning optic 130 coupled to the center turning optic 120 by an arm 410. The remote turning optic 130 may be mounted to a frame 420, or alternatively, may be entirely supported by the arm 410. The remote turning optic 130 is fixed to the center turning optic 120, so it rotates about the axis 180 with the center turning optic 120 to angularly align the turning optics 120, 130 with the devices 150. As the sockets 160 are equidistant from the center turning optic 120, the alignment between the remote turning optic 130 and the sockets 160 is determined by the angular position of the center turning optic 120. The concurrent testing of the imager devices 150 may proceed as described above with respect to FIG. 3 (i.e., serial illumination and parallel data processing).

Figure 5:
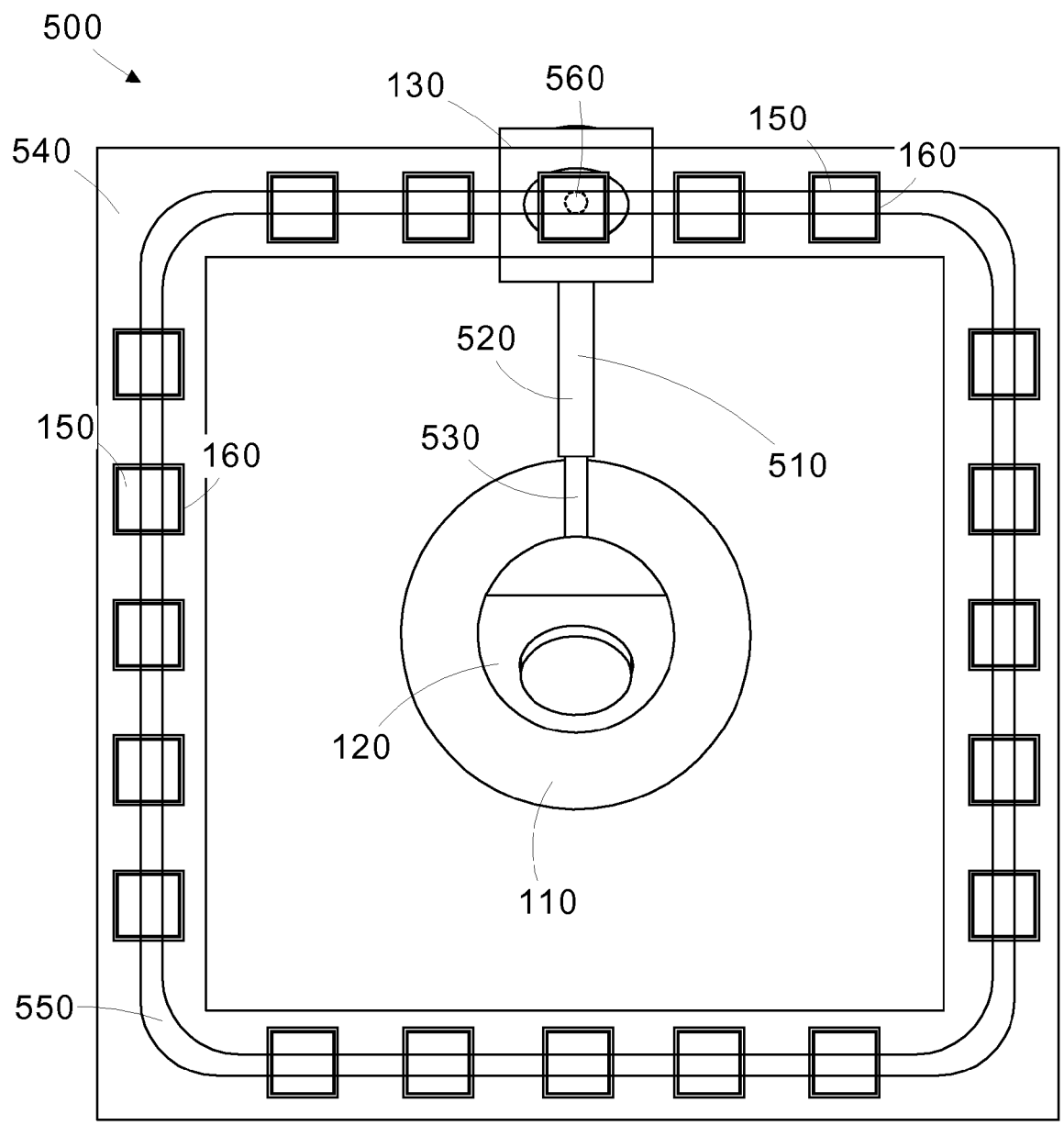
FIG. 5 is a diagram of an optical test system including a remote turning optic coupled to a central turning optic by a reciprocating arm.

Turning now to FIG. 5, yet another embodiment of an optical test system 500 is shown. The test system 500 of FIG. 5 is similar to the system 400 of FIG. 4 with the exception of the placement of the sockets 160 with respect to the center turning optic 120. The sockets 160 are arranged in a rectangular pattern with respect to the center turning optic 120. Conventional handling devices for mounting the imager devices 150 in the sockets 160 operate using a rectangular coordinate system. The remote turning optic 130 is coupled to the center turning optic 120 by a reciprocating arm 510. In one embodiment, the reciprocating arm 510 includes an outer sleeve 520 that cooperates with an inner sleeve 530 to allow the length of the arm 510 to change depending on the distance from the center turning optic 120 to the socket 160 holding the imager device 150 under test.

The length of the reciprocating arm 510 may be controlled using various techniques. In one embodiment, a frame 540 including a track 550 may be provided within which the remote turning optic 130 moves. A pin 560 on the bottom of the remote turning optic 130 may fit into the track 550. The layout of the track 550 follows the rectangular layout of the sockets 160. As the center turning optic 120 and remote turning optic 130 rotate to angularly align with a selected socket, the pin 560 and track 550 cooperate to extend or retract the reciprocating arm 510 to linearly align the remote turning optic 130 with the socket 160.

In other embodiments not employing the frame 540, a motor may be provided for positioning the reciprocating arm 510. A position counter may be provided for monitoring and controlling the amount of arm extension. A look-up table may be provided specifying the arm position and/or radial position for each socket. Alternatively, a sensor (e.g., optical or electrical) may be provided for detecting the position of the remote turning optic 130 with respect to the socket 160. After aligning the center turning optic 120 with the socket 160, the motor may start from a partially retracted position and extend until the sensor is triggered.

Figure 6:
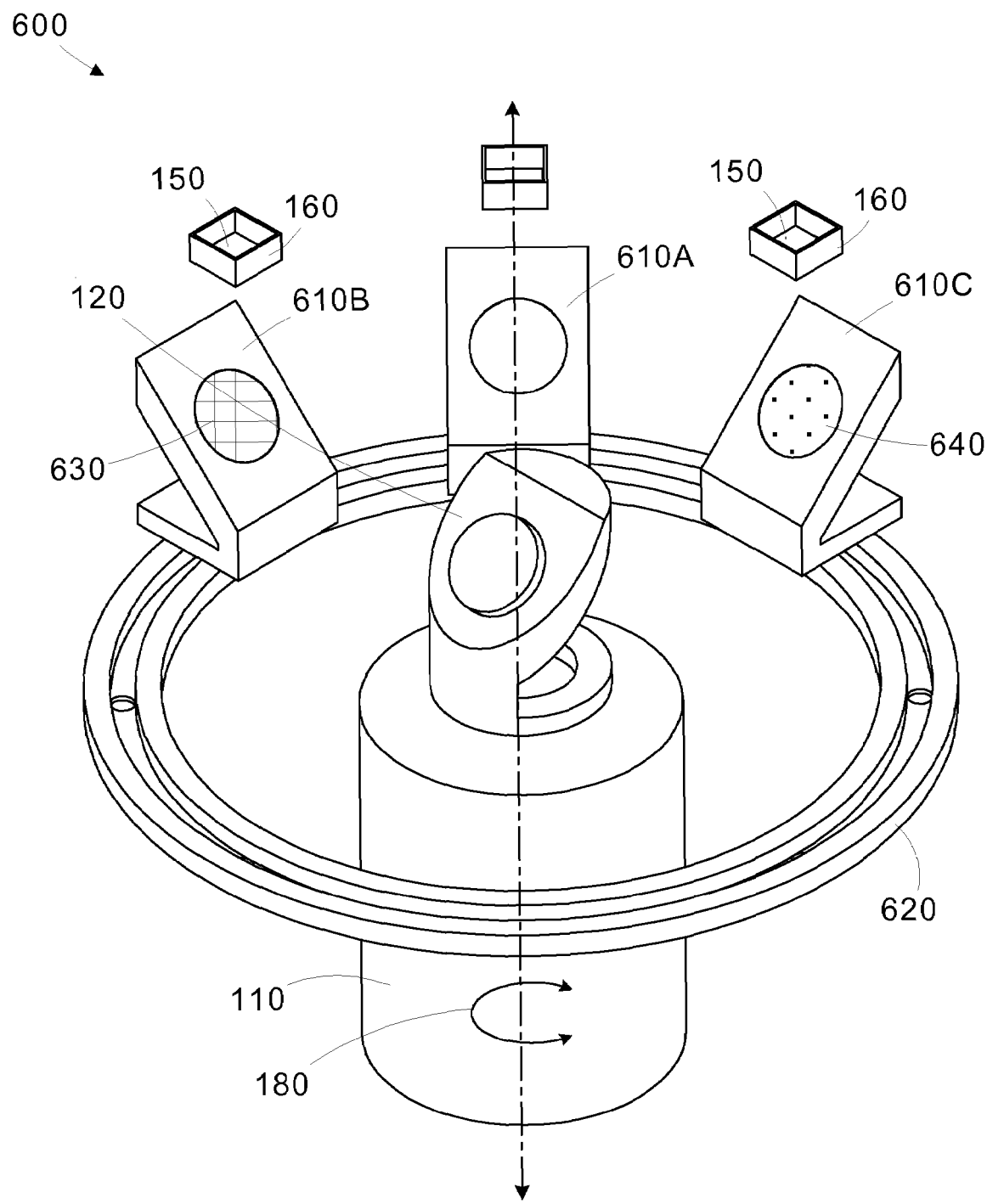
FIG. 6 is a diagram of an optical test system including remote turning optics with different optical altering properties.

Referring to FIG. 6, an embodiment of an optical test system 600 is shown including multiple remote turning optics 610A-C, each having different reflection characteristics. The remote turning optics 610A-C are mounted to a frame 620 that rotates independently around the same axis 180 as the center turning optic 120. This rotational independence allows different remote turning optics 610A-C to be aligned with different sockets 160. As illustrated in FIG. 6, the center turning optic 120 is aligned with the socket 160 above the remote turning optic 610C.

In the illustrated embodiment of FIG. 6, each of the remote turning optics 610A-C has different optical altering properties. For example, the remote turning optic 610A is standard in that it does not affect the projected light beam, the remote turning optic 610B imposes a pattern 630 on the image projected on the imager device 150, and the remote turning optic 610C includes a diffuser 640. Of course, additional remote turning optics may be provided with still other image altering properties, or multiple remote turning optics having the same properties may be provided.

By independently rotating the frame 620 and the center turning optic 120, different images may be projected on the imager devices 150. In this manner, each imager device 150 may be tested using a standard image, a patterned image, and a diffused image. To provide concurrent processing, the center turning optic 120 may start aligned with the remote turning optic 610A. After the patterned image capture, the center turning optic 120 may rotate to align with the remote turning optic 610B to initiate a standard image capture. While the standard image capture processing is progressing, the center turning optic 120 may rotate to align with the remote turning optic 610C to initiate a diffused image capture. Subsequently, the center turning optic 120 and the frame 620 may be aligned to different positions to allow the testing of the imager devices 150 with differing patterns until each imager device 150 has been tested with each optical pattern.

Figure 7:
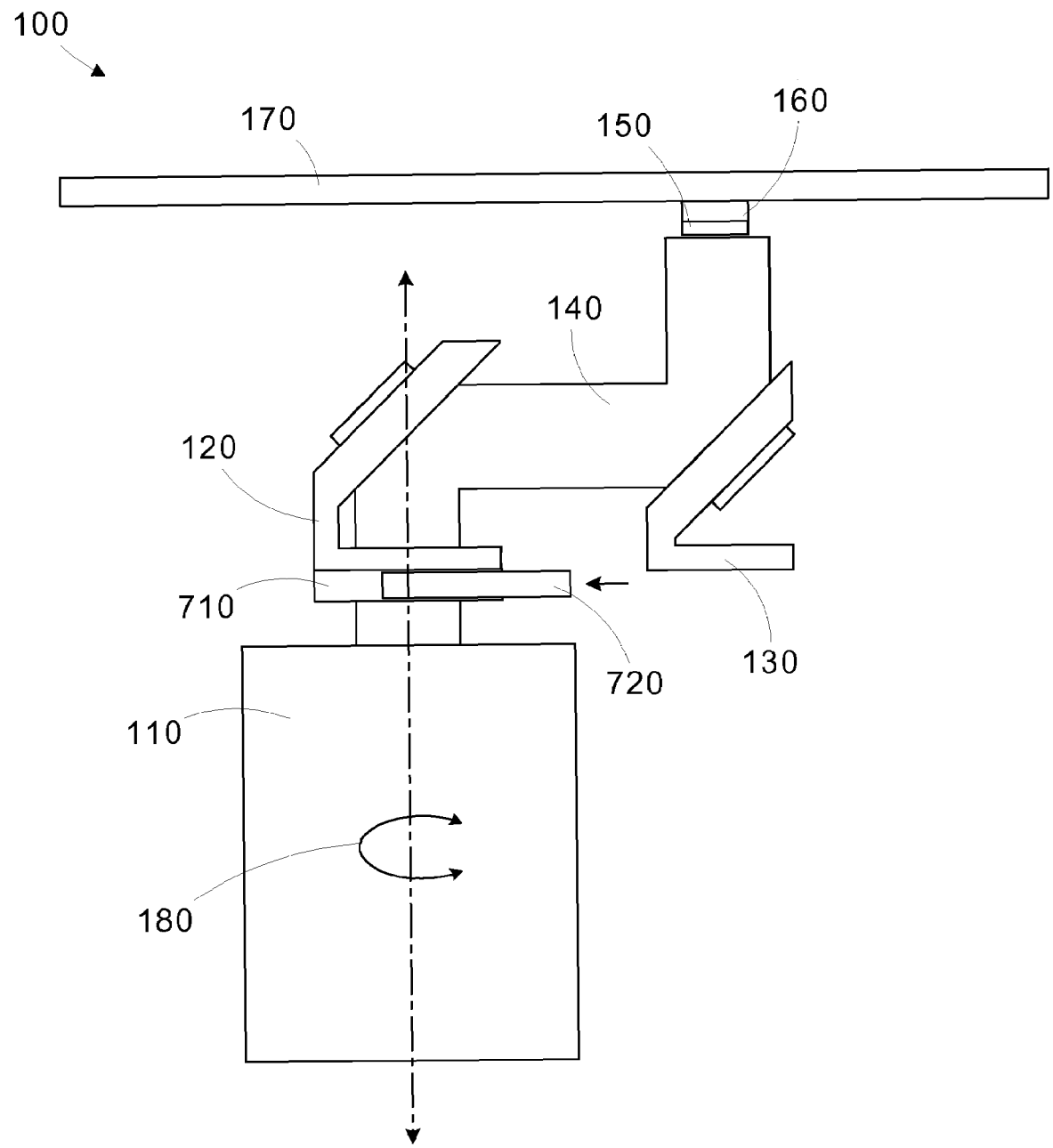
FIG. 7 is a diagram of an optical test system including an inline filter.

Turning now to FIG. 7, a diagram of an alternative embodiment an optical test system 700 is provided wherein the center turning optic 120 includes a housing 710 for receiving a filter 720. Similar to the embodiment of FIG. 6, the filter may alter the light beam 140 (e.g., by imposing a pattern or diffusing the light) to provide additional testing options. In the embodiment of FIG. 7, all of the imager devices 150 may be tested with a single pattern using the filter 720. The filter 720 may then be removed or replaced with a different type of filter to allow testing of the imager devices 150 with a different image. Although the housing 710 is illustrated as being mounted to the center turning optic 120, in some embodiments, the housing 710 may be mounted to the light source 110 or the remote turning optic.

One aspect of the present invention is seen in an optical test system including a light source, a first turning optic, and a second turning optic. The second turning optic is positioned proximate the light source and is operable to direct light from the light source to the first turning optic. The first turning optic is further operable to direct light from the second turning optic to illuminate one of a plurality of test regions for receiving devices under test. At least one of the first and second turning optics is movable to align the light generated by the light source with a selected test region.

Another aspect of the present invention is seen in a method for optically testing a device with light generated by a light source. A first turning optic is provided. A second turning optic positioned proximate the light source is provided. The second turning optic is operable to direct light from the light source to the first turning optic. The first turning optic is further operable to direct light from the second turning optic to illuminate one of a plurality of test regions for receiving devices under test. At least one of the first and second turning optics is moved to align the light generated by the light source with a selected test region.

The optical test system embodiments described herein allow the concurrent testing of multiple devices without requiring the use of a large, expensive light source. The ability to test higher numbers of devices concurrently reduces the time required to functionally test completed devices, thereby increasing throughput, efficiency, and ultimately, profitability.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

I claim:

1. An optical test system, comprising:
    a light source;
    a first turning optic; and
    a second turning optic positioned proximate the light source and being operable to direct light from the light source to the first turning optic, the first turning optic being further operable to direct light from the second turning optic to illuminate one of a plurality of test regions for receiving imaging devices under test, wherein at least one of the first and second turning optics is movable to align the light generated by the light source with a selected test region.

2. The system of claim 1, wherein the first turning optic operable to rotate about a first axis.

3. The system of claim 1, wherein the second turning optic is mounted to the light source.

4. The system of claim 1, wherein the first turning optic is fixed in position with respect to the second turning optic.

5. The system of claim 1, further comprising a plurality of turning optics, including the first turning optic, fixed in position with respect to the second turning optic, wherein each of the plurality of turning optics is associated with one of the test regions for receiving imaging devices under test and the second turning optic is movable to align with a selected one of the plurality of turning optics.

6. The system of claim 5, wherein the second turning optic is operable to rotate about a first axis to align with the selected one of the plurality of turning optics.

7. The system of claim 5, further comprising a support member, wherein each of the plurality of turning optics is mounted to the support member.

8. The system of claim 1, further comprising a member coupling the first turning optic to the second turning optic, the first and second turning optics being operable to rotate about a first axis to angularly align the first and second turning optics with the selected test region.

9. The system of claim 8, wherein the member comprises a reciprocating arm operable to linearly align the first turning optic with the selected test region.

10. The system of claim 9, further comprising a support member including a track for receiving the first turning optic and controlling a degree of extension of the reciprocating arm.

11. The system of claim 10, further comprising a motor operable to control a degree of extension of the reciprocating arm.

12. The system of claim 1, further comprising:
a support member, wherein the first turning optic is mounted to the support member and operable to rotate about a first axis; and
a third turning optic mounted to the support member and having an optical altering property, wherein the support member is operable to rotate about the first axis independent of the second turning optic to align one of the first and third turning optics with the selected test region.

13. The system of claim 12, wherein the optical altering property comprises at least one of a diffusing property and a pattern-imposing property.

14. The system of claim 1, further comprising a filter positioned in a path of a light beam generated by the light source.

15. The system of claim 14, further comprising a housing mounted to one of the first turning optic, the second turning optic, and the light source and operable receive the filter.

16. The system of claim 14, wherein the filter is operable to impose a pattern on the light beam.

17. The system of claim 14, wherein the filter is operable to diffuse the light beam.

18. An optical test system, comprising:
a light source;
a first plurality of turning optics, each turning optic being positioned proximate an associated test region; and
a rotatable turning optic positioned proximate the light source and being rotatable about a first axis to align with a selected one of the first plurality of turning optics and direct light from the light source to the selected turning optic, the selected turning optic being further operable to direct light from the rotatable turning optic to illuminate a first imaging device under test positioned in the associated test region.

19. An optical test system, comprising:
a light source;
a first turning optic; and
a second turning optic coupled to the first turning optic and positioned proximate the light source, the second turning optic being rotatable about a first axis to align the first turning optic to one of a plurality of test regions operable to receive imaging devices under test.

20. A method for optically testing a device with light generated by a light source comprising:
providing a first turning optic;
providing a second turning optic positioned proximate the light source and being operable to direct light from the light source to the first turning optic, the first turning optic being further operable to direct light from the second turning optic to illuminate one of a plurality of test regions for receiving imaging devices under test; and
moving at least one of the first and second turning optics to align the light generated by the light source with a selected test region.

21. The method of claim 20, further comprising rotating the second turning optic about a first axis to align with the first turning optic.

22. The method of claim 20, further comprising mounting the second turning optic to the light source.

23. The method of claim 20, further comprising fixing a position of the first turning optic with respect to the second turning optic.

24. The method of claim 20, further comprising:
providing a plurality of turning optics, including the first turning optic, fixed in position with respect to the second turning optic, wherein each of the plurality of turning optics is associated with one of the test regions for receiving imaging devices under test; and
moving the second turning optic to align with a selected one of the plurality of turning optics.

25. The method of claim 20, further comprising:
coupling the first turning optic to the second turning optic; and
rotating the first and second turning optics about a first axis to angularly align the first and second turning optics with the selected test region.

26. The method of claim 25, wherein first turning optic is coupled to the second turning optic by a reciprocating arm, and the method comprises controlling a degree of extension of the arm to linearly align the first turning optic with the selected test region.

27. The method of claim 20, further comprising:
mounting the first turning optic to a support member;
mounting a third turning optic to the support member, the third turning optic having an optical altering property;
rotating the support member about a first axis to align one of the first and third turning optics with the test region; and
rotating the second turning optic about the first axis independently of the support member to align the second turning optic with the one of the first and third turning optics aligned with the test region.

28. The method of claim 27, wherein the optical altering property comprises at least one of a diffusing property and a pattern-imposing property.

29. The method of claim 20, further comprising providing a filter positioned in a path of a light beam generated by the light source.

30. The method of claim 29, wherein the filter is operable to impose a pattern on the light beam.

31. The method of claim 29, wherein the filter is operable to diffuse the light beam.

32. The method of claim 20, further comprising operating a device under test positioned in the selected test region and illuminated by the light source.

* * * * *

UNITED STATES PATENT AND TRADEMARK OFFICE
CERTIFICATE OF CORRECTION

PATENT NO.       : 7,633,611 B2
APPLICATION NO.  : 11/458720
DATED            : December 15, 2009
INVENTOR(S)      : Dustin D. Inskeep It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this

Ninth Day of November, 2010

David J. Kappos
*Director of the United States Patent and Trademark Office*